US00PP30950P2

(12) United States Plant Patent
Kordes

(10) Patent No.: US PP30,950 P2
(45) Date of Patent: Oct. 22, 2019

(54) MINIATURE ROSE PLANT NAMED 'KORONE001'

(50) Latin Name: *Rosa hybrida*
Varietal Denomination: KORone001

(71) Applicant: W. KORDES' SÖHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES' SÖHNE ROSENSCHULEN GMBH & CO KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 15/998,224

(22) Filed: Jul. 19, 2018

(30) Foreign Application Priority Data

May 28, 2018 (QZ) ..... PBR 2018/1391

(51) Int. Cl.
*A01H 5/02* (2018.01)
*A01H 6/74* (2018.01)

(52) U.S. Cl.
USPC ..... Plt./122

(58) Field of Classification Search
USPC ..... Plt./110, 116, 122
See application file for complete search history.

(56) References Cited

U.S. PATENT DOCUMENTS

PP24,197 P2 * 1/2014 Kordes ..... A01H 6/749 Plt./122
PP25,004 P2 10/2014 Kordes

* cited by examiner

*Primary Examiner* — Susan McCormick Ewoldt
*Assistant Examiner* — Karen M Redden
(74) *Attorney, Agent, or Firm* — Buchanan Ingersoll & Rooney PC

(57) ABSTRACT

A new and distinct variety of Miniature Rose Plant, herein referred to by its cultivar name, 'KORone001', is provided which forms attractive, double, red colored blossoms. The vegetation is vigorous and the growth habit is upright. Attractive ornamental foliage is formed. The new variety is particularly well suited for providing distinctive ornamentation in the landscape.

1 Drawing Sheet

Botanical/commercial classification:
Latin name—*Rosa hybrida.*
Common name—Miniature Rose Plant.
Varietal denomination—'KORone001'.

CROSS-REFERENCE TO RELATED APPLICATIONS

This application claims priority to Plant Breeders' Right Application Number 2018/1391, which was filed at Community Plant Variety Office in the European Union on May 28, 2018, the contents of which are hereby incorporated by reference for all purposes.

SUMMARY OF THE INVENTION

The new variety of *Rosa hybrida* Miniature Rose Plant of the present invention was created during 2013 at Offenseth-Sparrieshoop, Germany by artificial pollination wherein two parents were crossed which previously had been studied in the hope that they would contribute the desired characteristics. The female parent (i.e., seed parent) of the new variety was an unnamed seedling (non-patented in the United States). The male parent (i.e., pollen parent) of the new variety was the 'KORpot028' variety (U.S. Plant Pat. No. 25,004).

The parentage can be summarized as follows:

unnamed seedling x 'KORpot028'

The seeds resulting from the above pollination were sown and small plants were obtained which were physically and biologically different from each other. Selective study resulted in the identification of a single plant of the new variety.

It was found that the new Miniature Rose Plant of the present invention possesses the following combination of characteristics:

(a) forms attractive, double, red colored blossoms,
(b) exhibits an upright growth habit,
(c) forms vigorous vegetation, and
(d) forms attractive ornamental foliage.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the unnamed seedling seed parent exhibits a different flower color, a different growth habit, and smaller flowers compared to the new variety. Additionally, the 'KORpot028' variety (i.e., pollen parent) exhibits an upright to bushy growth habit, whereas the new variety displays an upright growth habit. Also, the 'KORpot028' variety displays flowers of a different color and smaller flowers compared to the new variety. Moreover, the new variety can be readily distinguished from non-parental related similar varieties. For example, the 'Meilavio' variety (U.S. Plant Pat. No. 10,845) displays flowers which have a shorter duration, more petals, and are less fragrant compared to the new variety. In addition, the 'KORscamer' variety (U.S. Plant Pat. No. 24,197) displays flowers with a lower petal count and are less fragrant compared to the new variety.

The new variety has been found to undergo asexual propagation in Klein Offenseth-Sparrieshoop, Germany by a number of routes such as vegetative cuttings. Asexual propagation techniques in Germany, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

The new variety has been named 'KORone001'.

BRIEF DESCRIPTION OF THE PHOTOGRAPHS

The accompanying photograph shows, as nearly true as it is reasonably possible to make the same in color illustrations of this character, a typical specimen of the new variety. The illustrated rose plant of the new variety was approximately twelve weeks of age and was observed at Klein Offenseth-Sparrieshoop, Germany while growing indoors on its own roots in 6.0 cm containers.

FIG. 1—illustrates a specimen of a blossom.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on the observation of a one-year-old specimen of the new variety, observed during February, while growing in a one-gallon container on its own roots in a greenhouse at Cochranville, Pa.

Class: Miniature Rose Plant.

Plant:

*Habit*.—Very upright.

*Height*.—Approximately 50.0 cm on average.

*Width*.—Approximately 30.0 cm on average.

Branches:

*Stem color*.—Immature stems: commonly near Yellow-Green Group 144A. Mature stems: commonly near Greyed-Brown Group N199B.

*Stem texture*.—Immature stems: glabrous. Mature stems: smooth to rough where the wood is becoming harder.

*Main stem length*.—Approximately 50.0 cm on average.

*Secondary stem length*.—Approximately 22.0 cm on average.

*Thorns*.—Number approximately 8 thorns per 5.0 cm of stem length on average. Young thorns: amount is moderate, length is approximately 4.0 mm on average, width is approximately 1.0 mm at point of attachment on average, and color is commonly near Greyed-Orange Group 167D. Old thorns: amount is moderate, length is approximately 5.0 cm on average, width is approximately 1.0 mm at point of attachment on average, and color is commonly near Brown Group 200B.

Foliage:

*General appearance*.—Ornamental.

*Young foliage*.—Upper surface color commonly near Green Group 137A suffused with near Greyed-Orange Group 166A and near Greyed-Purple Group 183A; and venation of near Greyed-Purple Group 183A. Under surface color: commonly near Green Group 137C suffused with near Greyed- Purple Group 183A; and venation of near Greyed-Purple Group 183D.

*Old foliage*.—Upper surface color commonly near Green Group 139A with indistinguishable venation. Under surface color: commonly near Green Group 138A with venation of near Green Group 138B.

*Petiole*.—Upper surface: texture is smooth; color is commonly near Yellow-Green Group 144A. Under surface: texture is mostly smooth with sparse prickles and color is commonly near Yellow-Green Group 146B. Length: approximately 4.5 cm on average.

*Rachis*.—Color: upper surface is commonly between near Green Group 143C and Green Group 143A, and under surface is commonly near Green Group 143C. Size: length is approximately 10.0 cm on average. Surface texture: smooth.

*Stipules*.—Length: approximately 1.5 cm on average. Width: approximately 5.0 mm on average. Margin: entire to erose. Color: upper surface is commonly near Yellow-Green Group 144A and under surface is commonly near Yellow-Green 144B.

*Leaf margin*.—Serrate.

*Glossiness of upper side of leaf*.—Semi-glossy.

Leaflets:

*Number*.—3, 5, and 7.

*Arrangement*.—Odd-pinnate.

*Shape*.—Ovate; apex is acute; and base is rounded.

*Venation pattern*.—Reticulate.

*Texture*.—Upper surface is smooth; under surface is smooth.

*Terminal leaflet*.—Length is approximately 6.0 cm on average; width is approximately 3.7 cm on average; margin undulation is weak; and the glossiness intensity of the upper surface is moderate.

*Lower leaflets*.—Length is approximately 3.5 cm on average and width is approximately 2.2 cm on average.

5-*leaflet leaf*.—Length is approximately 12.5 cm on average and width is approximately 9.0 cm on average.

Inflorescence:

*Number of flowers*.—About 1 to 3 blooms on average on a plant at once.

*Number of blossoms per stem*.—Typically 1 bloom per stem on average.

*Type*.—Single.

*Peduncle*.—Color: commonly Yellow-Green Group 144A. Diameter: approximately 3.0 mm on average. Length: approximately 7.0 cm on average. Surface texture: glabrous. Strength: strong.

*Sepals*.—Number: commonly 5. Upper surface color and texture: covered in short pubescence and color is commonly near Yellow-Green Group 144A. Under surface color and texture: puberulent and color is commonly near Yellow-Green Group 144A. Size: length is approximately 2.5 cm on average and width is approximately 6.0 mm on average. Margin: entire with occasional extensions on two or three sepals measuring approximately 7.0 mm in length and approximately 3.0 mm in width. Shape: lanceolate; apex is acute to aristate; and base is truncate or flat as it joins the receptacle.

*Bud*.—Shape: globular. Size: length is approximately 2.3 cm on average; width is approximately 1.7 cm on average. Color (when opening): commonly near Red Group 46A.

*Flower*.—Form: double, cuplike. Profile: flat. Height: approximately 5.0 cm on average. Diameter: approximately 10.0 cm on average. Duration: flower lasts on the plant for 35 days on average.

*Fragrance*.—Light sweet fragrance.

*Petal*.—Number: approximately 65 on average. Drop: good. Length: inner petals are approximately 3.5 cm on average; outer petals are approximately 4.2 cm on average. Width: inner petals are approximately 2.5 cm on average; outer petals are approximately 4.5 cm on average. Shape: overall shape is broadly obovate; apex is rounded; and base is cuneate. Margin: entire. Margin undulation: strong. Texture: upper and lower surfaces are glabrous. Color with first and fully open: upper surface is commonly near Red-Purple Group N57A with basal spot of commonly near Yellow Group 7D; and under surface is commonly near Red-Purple Group 58C with basal spot of commonly near Yellow Group 4D. Color when fading: upper surface is commonly near Red-Purple 58B with basal spot of near Yellow Group 10D; under surface is commonly near Red-Purple Group 65C with basal spot of near Yellow Group 11D.

*Petaloids*.—Number: 5 on average per flower. Color: upper surface is commonly near Red- Purple Group N57A with a basal spot of near Yellow Group 7D; under surface is commonly near Red-Purple Group 58C with a basal spot of near Yellow Group 4D. Length: approximately 3.2 cm on average. Width: approximately 2.0 cm on average. Texture: smooth. Margins: variable, entire to erose. Shape: variable, oblong and mostly curving inward. Apex: round. Base: cuneate.

*Stamen*.—Number: approximately 115 on average. Anthers: number is about 115; color is commonly near is commonly near Greyed-Orange Group 164B; shape is oval; and length is approximately 2.5 mm on average. Filaments: length is approximately 7.0 mm on average and color is commonly near Greyed-Orange Group 164D.

*Pistils*.—Arrangement: separate and free. Number: approximately 139. Style: color is commonly near Red-Purple Group 58B and some exhibiting a small hint of Yellow Group 11C at the base of the stigma; length is less than 6.0 mm on average. Stigma: color is commonly near Greyed- Yellow Group 162B; diameter is commonly less than 1.0 mm on average; and shape is fan shaped.

*Ovary*.—Length is approximately 2.0 mm on average, width is approximately 1.0 mm on average, and color is commonly near White Group 155D.

*Receptacle*.—Achenes stand on the bottom and wall; diameter is approximately 1.3 cm on average, shape is round, color is commonly near Yellow-Green Group 144A, and surface texture is smooth.

*Pollen*.—None observed.

*Hips/seed*.—None observed.

Development:

*Vegetation*.—Dark green, vigorous and strong; the amount of vegetation growth per season is minimal.

*Blossoming*.—Produces few large individual blooms at a given time; will rebloom again in the same season.

*Hardiness*.—Unknown.

*Resistance to disease*.—Good resistance for *Botrytis* (*Botrytis cinerea*) disease under normal greenhouse growing conditions in Cochranville, Pa.

Plants of the 'KORone001' variety have not been observed under all possible environmental conditions to date. Accordingly, it is possible that the phenotypic expression may vary somewhat with changes in light intensity and duration, cultural practices, and other environmental conditions.

I claim:

1. A new and distinct Miniature Rose Plant characterized by the following combination of characteristics:

(a) forms attractive, double, red colored blossoms, (b) exhibits an upright growth habit, (c) forms vigorous vegetation, and (d) forms attractive ornamental foliage;

substantially as herein shown and described.

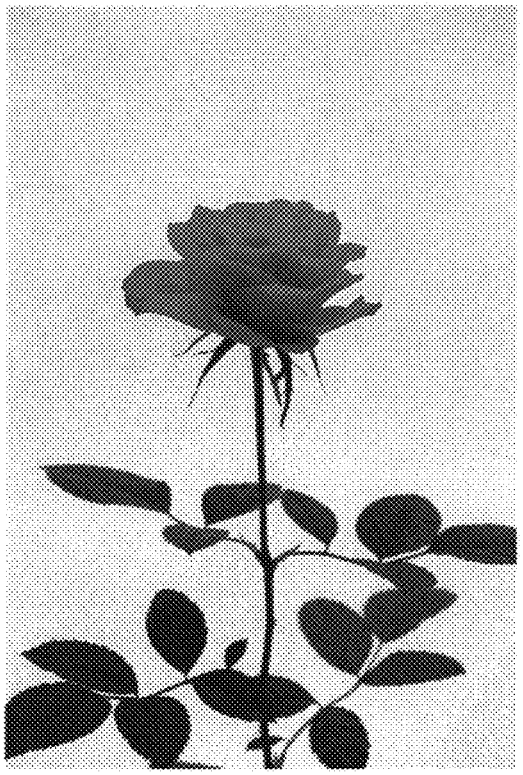

* * * * *